US012514968B2

(12) United States Patent
Batiste

(10) Patent No.: US 12,514,968 B2
(45) Date of Patent: Jan. 6, 2026

(54) AV FLOW RESTRICTORS

(71) Applicant: Stan Batiste, Granite Bay, CA (US)

(72) Inventor: Stan Batiste, Granite Bay, CA (US)

( * ) Notice: Subject to any disclaimer, the term of this patent is extended or adjusted under 35 U.S.C. 154(b) by 0 days.

(21) Appl. No.: 18/202,010

(22) Filed: May 25, 2023

(65) Prior Publication Data

US 2023/0293800 A1 Sep. 21, 2023

Related U.S. Application Data

(62) Division of application No. 16/659,386, filed on Oct. 21, 2019, now Pat. No. 12,042,592.

(60) Provisional application No. 62/748,280, filed on Oct. 19, 2018.

(51) Int. Cl.
*A61M 1/36* (2006.01)

(52) U.S. Cl.
CPC ........ *A61M 1/3655* (2013.01); *A61M 1/3661* (2014.02); *A61M 2205/0216* (2013.01); *A61M 2205/3334* (2013.01); *A61M 2206/10* (2013.01)

(58) Field of Classification Search
CPC .............. A61M 1/3655; A61M 1/3661; A61M 2205/0216; A61M 2205/3334; A61M 2206/10; A61M 2206/20; A61F 2250/001; A61F 2250/0039; A61F 2/90; A61F 2002/068; A61F 2250/0071
See application file for complete search history.

(56) References Cited

U.S. PATENT DOCUMENTS 3,826,257 A 7/1974 Buselmeier
4,153,640 A 5/1979 Nichols et al.
4,256,094 A 3/1981 Kapp et al.
4,549,879 A 10/1985 Groshong et al.
4,562,597 A 1/1986 Possis et al.
5,713,859 A 2/1998 Finch, Jr. et al.
5,797,879 A 8/1998 DeCampli
5,800,514 A 9/1998 Nunez et al.
5,849,036 A 12/1998 Zarate
6,045,496 A 4/2000 Pacella et al.
(Continued)

FOREIGN PATENT DOCUMENTS

WO WO 2009/152488 6/2009

OTHER PUBLICATIONS

Stanley Batiste, co-pending, unpublished U.S. Appl. No. 16/685,982, filed Nov. 15, 2019.

*Primary Examiner* — Rebecca E Eisenberg
*Assistant Examiner* — Alessandro R Del Priore
(74) *Attorney, Agent, or Firm* — The Powers IP Law Firm

(57) ABSTRACT

A shunt comprising a flexible tube having a first, and a second end, and a central opening, having a first diameter that extends from the first end to the second end. The shunt also includes one or more restrictor bands having a second diameter around the flexible tube. The one or more restrictor bands are located between the first end and the second end of the flexible tube and the second diameter is less than the first diameter such that the restrictor band forms a restriction. The restrictor band is expandable between a first position and a second position. The restrictor band may have fracturable sections configured to fracture in responds to pressure thereby increasing a diameter of the one or more restrictor bands to a diameter greater than the second diameter. The one or more restrictor bands may comprise restrictor bands of at least two different inner diameters.

16 Claims, 8 Drawing Sheets

(56) References Cited

U.S. PATENT DOCUMENTS

| | | | |
|---|---|---|---|
| 6,056,717 A | 5/2000 | Finch et al. | |
| 6,146,414 A | 11/2000 | Gelman | |
| 6,261,257 B1 | 7/2001 | Uflacker et al. | |
| 6,338,724 B1 | 1/2002 | Dossa | |
| 6,371,981 B1 | 4/2002 | Yang et al. | |
| 6,461,321 B1 | 10/2002 | Quinn | |
| 6,585,762 B1 | 7/2003 | Stanish | |
| 6,598,278 B2 | 7/2003 | Chen et al. | |
| 7,025,741 B2 | 4/2006 | Cull | |
| 7,108,673 B1 | 9/2006 | Batiste | |
| 7,540,859 B2 | 6/2009 | Claude et al. | |
| 7,811,298 B2 | 10/2010 | Birk | |
| 7,833,186 B1 | 11/2010 | Batiste | |
| 8,096,967 B2 | 1/2012 | Radojicic | |
| 8,216,174 B2 | 7/2012 | Wilk et al. | |
| 8,551,033 B1 | 10/2013 | Batiste | |
| 8,684,960 B2 | 4/2014 | Batiste et al. | |
| 8,715,218 B2 | 5/2014 | Batiste et al. | |
| 9,907,900 B1 | 3/2018 | Batiste et al. | |
| 2003/0114918 A1 | 6/2003 | Garrison | |
| 2004/0249334 A1 | 12/2004 | Cull | |
| 2006/0095114 A1* | 5/2006 | Hartley | A61F 2/07 623/1.16 |
| 2006/0224100 A1 | 10/2006 | Gertner | |
| 2006/0229548 A1 | 10/2006 | Cull | |
| 2007/0142907 A1 | 6/2007 | Moaddeb | |
| 2011/0015723 A1 | 1/2011 | Batiste et al. | |
| 2011/0125244 A1 | 5/2011 | Roeder | |
| 2011/0172692 A1* | 7/2011 | Wu | A61M 1/3655 606/191 |
| 2018/0078366 A1* | 3/2018 | Sievers | A61F 2/2418 |
| 2019/0125517 A1 | 5/2019 | Cully | |
| 2023/0201014 A1* | 6/2023 | Sirhan | A61F 2/915 623/1.16 |

* cited by examiner

FIG. 1
FIG. 2A
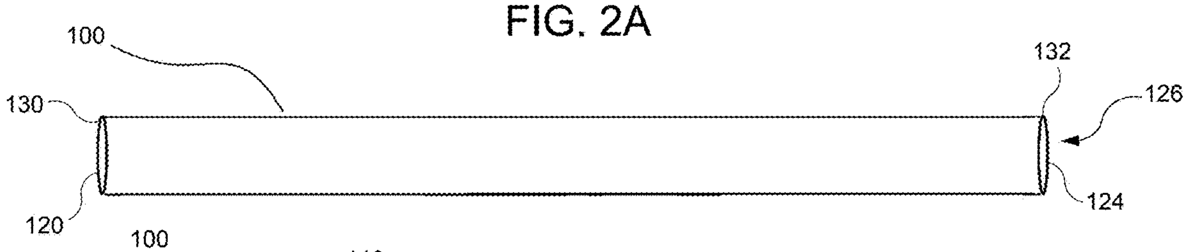
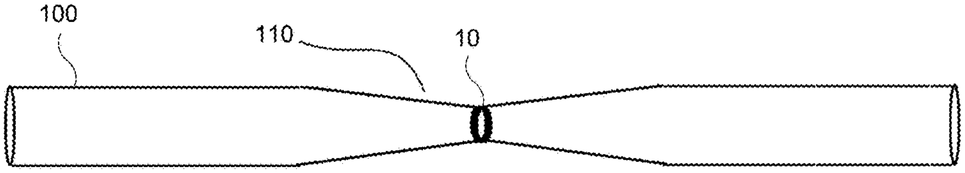
FIG. 2B
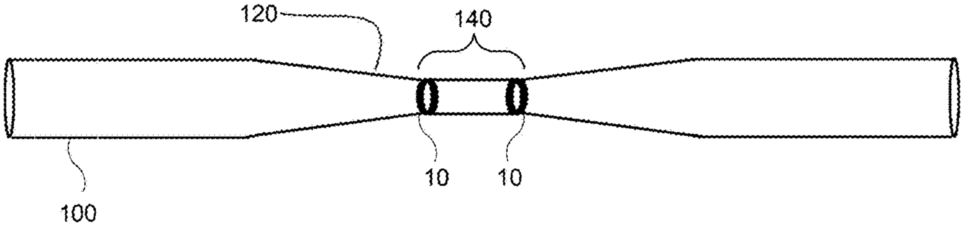
FIG. 2C

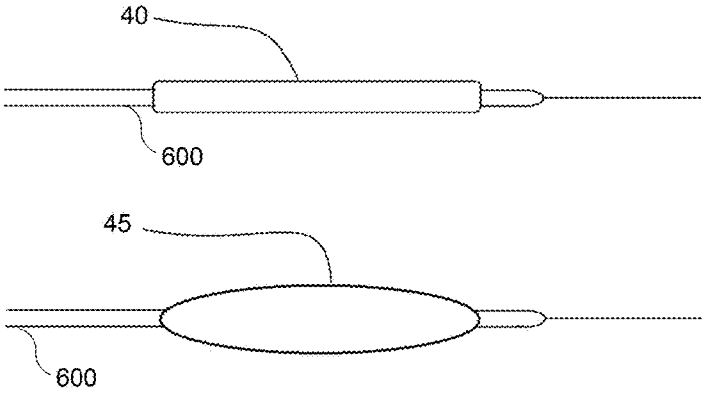
FIG. 6
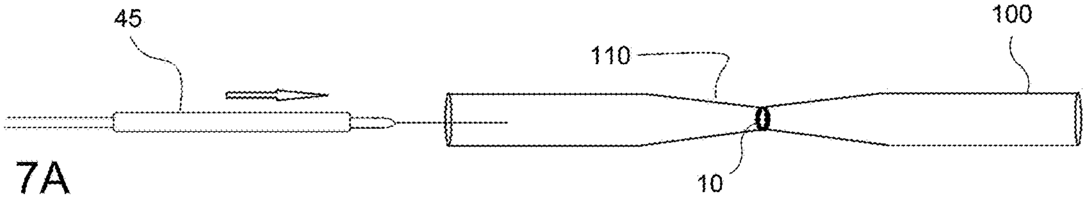
FIG. 7A
FIG. 7B
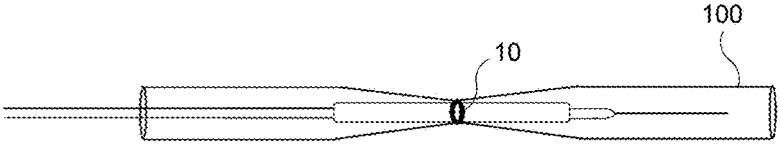
FIG. 7C
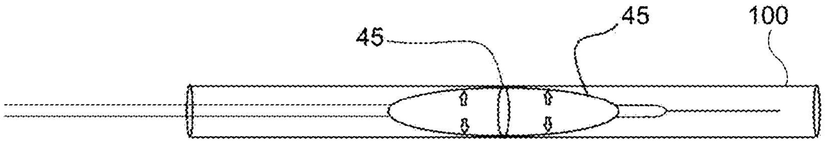
FIG. 7D
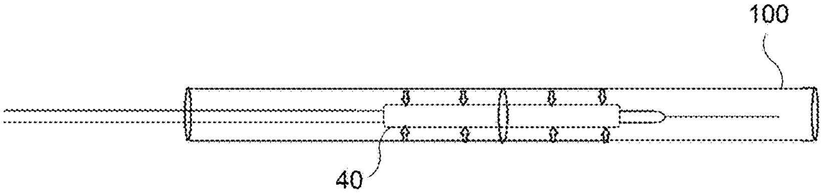
FIG. 7E
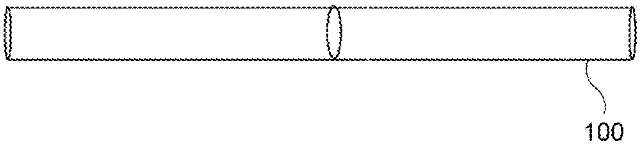

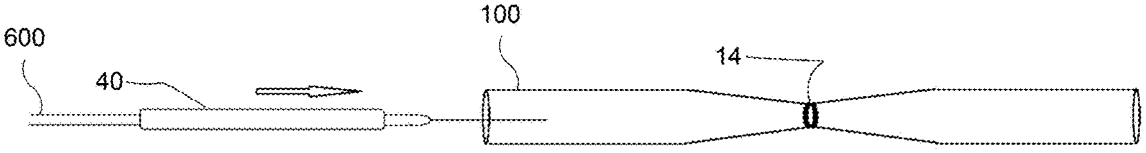
FIG. 10A
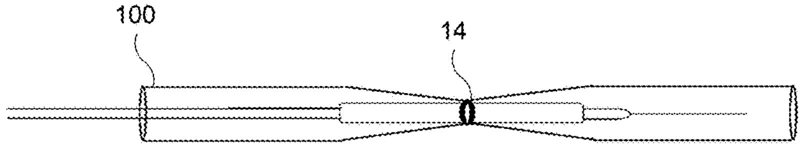
FIG. 10B
FIG. 10C
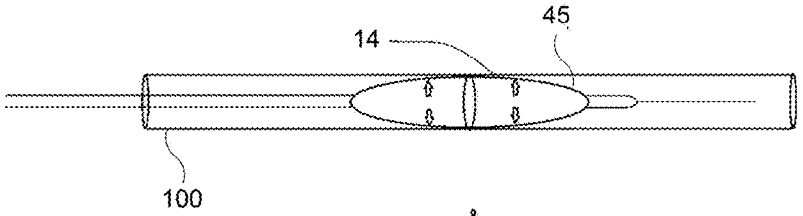
FIG. 10D
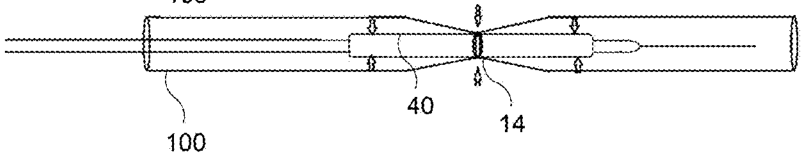
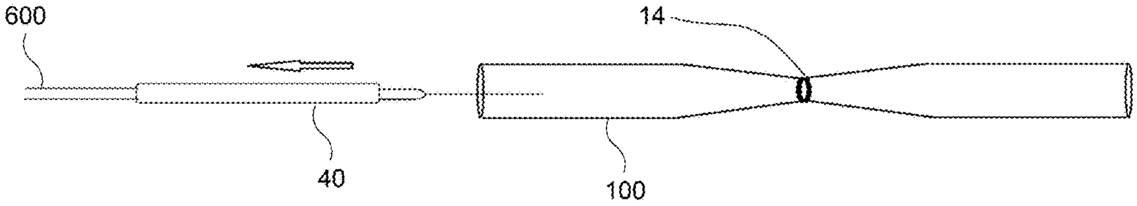
FIG. 10E

AV FLOW RESTRICTORS

1. FIELD OF THE INVENTION

The field of the invention relates generally to venous grafts and in particular to flow restrictors created to modify the flow dynamics.

2. BACKGROUND OF THE INVENTION

There are currently more than 400,000 patients in the United States with end-stage renal disease (ESRD) and many times more throughout the world. Patients with ESRD have lost their normal kidney function and as a result require dialysis to substitute the function of the kidney cleansing the blood.

The challenge with providing hemodialysis is maintaining access to large volumes of blood when our bodies constantly fight medical attempts to keep dialysis access available. Currently there are three ways to provide hemodialysis: dialysis catheters, arterial venous fistulas, and arterial venous grafts. All current methods are however limited, providing access for only short periods of time. This requires patients to have repeated invasive procedures for survival. Additionally, with AV shunt devices to provide dialysis there is blood shunted away from the hand and continuous loss of cardiac output. This can lead to unwanted medical consequences. To overcome the drawbacks of the prior art, the disclosed design extends the life of the dialysis graft and well as decreasing the loss of blood to the extremity while also maintaining the cardiac output, thus prolonging the lives of patients.

SUMMARY

Arterial-Venous fistulas and grafts termed AV shunts are the most effective means to provide large volume blood access for hemodialysis patients. Patency rates however are relatively low as both means of AV shunts occlude primarily because normal vein stenosis occurs at the output of the graft as a result of high pressure, pulsation and flow rates. An additional limitation of current AV shunts is the stealing of blood from the artery that would normally feed the distal portion of the extremity, such as the finger. This blood is shunted through the AV fistula back to the heart, thus bypassing the lower portion of the extremity. This creates two issues, the first is distal extremity ischemia that often results in finger loss through amputation and the constant loss of cardiac output making the heart work much harder, continuously, than it normally would without a shunt. One proposed means and method to surgically treat this is to create a vascular band around the fistula or graft creating a surgical flow restrictor. Another method described in prior Batiste designs is a manufactured flow restrictor with the body of the graft or fistula. Other Batiste patents describe several such devices including preformed restrictor, balloon restrictors and restrictors using cellular materials among several others. U.S. Pat. No. 8,715,218 issued to Batiste entitled Self Adjusting Venous Equalizing Graft and Endothelial Lining Therefore issued on May 6, 2014 is incorporated by reference in its entirety therein.

This invention provides an innovative means to create a flow restrictor within an AV shunt that can be modified if hemodynamics or patient clinical condition changes. The design utilizes a mechanical band that functions to selectively and controllably restrict the inner diameter of the AV shunt. The innovative band may contain several different properties as described including several embodiments including a pliable design that once stretched with a balloon stays expanded completely eliminating the stenosis, a fracturable band which breaks at predetermined sites in order to release the flow restriction narrowing and eliminating the narrowing, and an elastic design which reforms the original flow restrictor configuration once the balloon therapy is removed. The expandable, fracturable and elastic flow restrictors can be placed prior to shunt surgical placement or via percutaneous endovascular placement as described herein.

Disclosed herein is a shunt having a flexible tube which has a first and second end, and a central opening with a first diameter extending from the first to the second end. The flexible tube has one or more restrictor bands which have a second diameter around the flexible tube. The restrictor band is located between the first and second end of the flexible tube, and the second diameter is less than the flexible tube's first diameter.

In one embodiment the shunt described above is an arterial venous shunt (AV shunt) which may be configured to have a restrictor band that expands between a first and a second position. The restrictor band may include sections that are configured to fracture (i.e., fracturable sections) in response to outward pressure thereby increasing a diameter of the one or more restrictor bands to a diameter greater than the second diameter. In one or more embodiments, the one or more restrictor bands in the AV shunt have at least two different inner diameters.

The AV shunt's tube length has an inlet end, an outlet end, and a central opening which extends from the inlet to the outlet ends such that central opening has a first diameter. In this embodiment, at least one band extends around a portion of the tube length and is located between the ends. The bands create a reduced diameter section of a second diameter that is adjustable from the second diameter, which is less than the first diameter to a third diameter which is greater than the second diameter. The AV shunt's third diameter may be the same as the first diameter.

The AV shunt's band may be further expandable from the third diameter to a fourth diameter, the fourth diameter being greater than the third diameter. In some embodiments, the band also has sections which are configured to fracture in response to outward pressure thereby increasing the band from the second diameter to the third diameter and may further contain two or more restrictor bands of at least two different inner diameters.

In one configuration, the tube functioning as an AV shunt, has a central opening with a first diameter extending from both the inlet and outlet ends. In one embodiment, the at least one band, has a second diameter which extends around the tube and is located between the inlet end and the outlet end, that creates a reduced diameter section in the tube such that the band is configured to expand in response to outward pressure and increase its diameter to adjust from the second diameter to a third diameter and then maintain the third diameter after the outward pressure is removed from the band. The amount of increase in diameter of the band is responsive to an amount of outward pressure. The band may be manufactured from elastic material which does not return to its original shape when expanded. In this embodiment, the inlet end of the AV shunt is configured to be connected to an artery, while the outlet end is configured to be connected to a vein. In other embodiments, multiple bands made from a fractionable material having differing diameters are arranged on one tube and consist of two sets of opposing mirrored sets of bands.

Other systems, methods, features and advantages of the invention will be or will become apparent to one with skill in the art upon examination of the following figures and detailed description. It is intended that all such additional systems, methods, features and advantages be included within this description.

BRIEF DESCRIPTION OF THE DRAWINGS

FIG. 1 is an illustration of a short flow restrictor and long flow restrictor.

FIGS. 2A, 2B, and 2C are a linear section of an AV graft (tube) and grafts with flow restrictors applied.

FIG. 6 is a collapsed (unexpanded) and expanded balloons.

FIG. 7A is an illustration of a collapsed balloon advancing into graft with short restrictor.

FIG. 7B is an illustration of a balloon positioned within the short restrictor.

FIG. 7C is an illustration of balloon inflated expanding restrictor.

FIG. 7D is an illustration of balloon deflated.

FIG. 7E is an illustration of balloon removed and expanded flow restrictor.

FIG. 10A is an illustration of a deflated balloon advancing into flow restrictor 10*b*.

FIG. 10B is an illustration of a deflated balloon within flow restrictor.

FIG. 10C is an illustration of a balloon expanded within flow restrictor.

FIG. 10D is an illustration of a balloon deflated and elastic restrictor.

FIG. 10E is an illustration of balloon removal and elastic restrictor regaining shape.

DETAILED DESCRIPTION OF THE PREFERRED EMBODIMENTS

Figure 3:
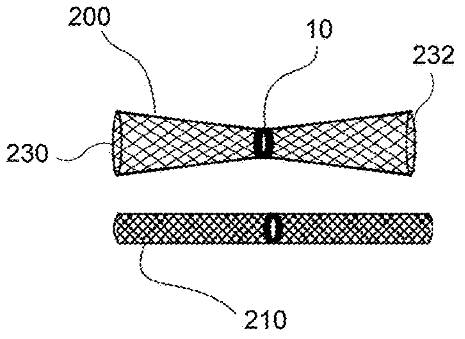
FIG. 3 is a short flow restrictor on a stent expanded and collapsed.

In one or more embodiments the invention utilizes a band to create external pressure on elements in order to narrow the inner lumen of a dialysis shunt thereby creating a stenosis that acts as a flow restrictor. The restricted flow then creates the perfect hemodynamic conditions within the shunt helping to eliminate shunt failure and improve flow to the extremities while decreasing cardiac output. As shown in FIG. 1 there are two sizes of bands or restrictor length represented; short (10) and long (20). Bands of different sizes may be used, such as wider versions shown in FIG. 13. It is also contemplated that that the long restrictor length may be formed by two bands 10, one at each end of the narrowed restrictor area, or multiple bands spaced for form the narrowing. The restrictor bands can be composed of materials that have the properties of expandable, fracturable and elastic. In one embodiment the restrictor is able to be expanded in diameter and also be reduced in diameter.

FIG. 2A illustrates an example tube 100 that may be used to form the shunt. The term shunt and graft may be used interchangeably herein. The tube 100 has an outer wall and an inner opening 126 that extends through the tube. The tube has an inlet end 130 (first end) that receives blood flow and an outlet end 132 (second end) that is for an outflow of blood. The tube 100 may be of different diameters to match the diameter of a vessel to which the tube will connect. It is contemplated that in one embodiment the inlet end is configured to connect to an artery while the outlet end is configured to connect a vein. The tube 100 may be any length and may be trimmed to cut to a suitable length. It is also contemplated that bands 10 may be manufactured with bands on the tube 100 or the bands may be placed on the tube at the desired location just prior to or during a medical procedure.

FIG. 2B illustrates the restrictor band 10 deployed on the outside of the hollow member (tube 100) of the arterial venous graft that is surgically placed within a patient. Once placed in a patient, blood flow through the graft will be limited due to the restriction 110 thereby improving conditions while maintaining the ability to have dialysis. The conditions that are improved include, but are not limited to, a reduction or elimination of normal vein stenosis at the output of the graft and stealing of blood from the artery.

FIG. 2C illustrates an embodiment with two bands 10 on the tube 100 to create a longer restricted region 140. One or more additional bands may be placed in the restricted region 140 to maintain the narrowing of the restricted region.

FIG. 3 illustrates an endovascular stent with a restrictor band. The stent 200 is shown in a contracted and expanded position. As shown, the stent 200 is provided with a restrictor band 10. The stent 200 has a first end 230 and a second end 232 and is configured to be placed inside a blood vessel of a patient. The short flow restrictor 10 on a stent expanded and collapsed 210 is shown. Endovascular stents are understood by those of ordinary skill in the art and as such they are not described in detail herein. The restrictor band in the stent 200 serves the same purpose as when used in connection with a shunt.

Figure 4:
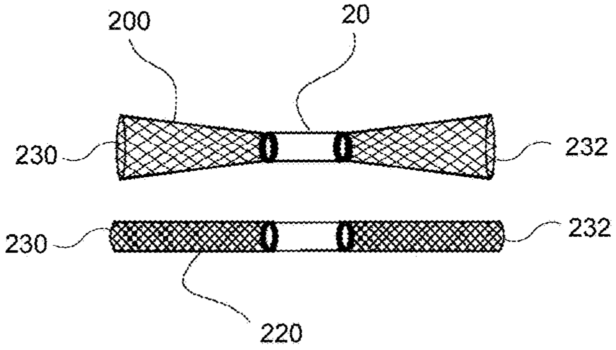
FIG. 4 is a long flow restrictor on a stent expanded and collapsed.

FIG. 4 illustrates the restricted section 20 placed on the outside portion of an endovascular stent 200 both within the collapsed position and the deployed expanded position. As with FIG. 3, the method of placement is similar to traditional stent placement where percutaneous access is first gained, followed by wire access, followed by collapsed stent advancement to the desired location in the vessel. Once positioned, the stent 200 is deployed. With the restrictor bands 10 in place, the stents outer portions (ends 230, 232) will open to oppose the vessel wall. The restrictor located in the middle, or between the ends, or away from the ends, will create radial pressure within the central portion of the stent prohibiting its central expansion, thereby creating a restriction. This restrictor will maintain a narrowing, creating the desired hemodynamic effects.

Figure 5A:
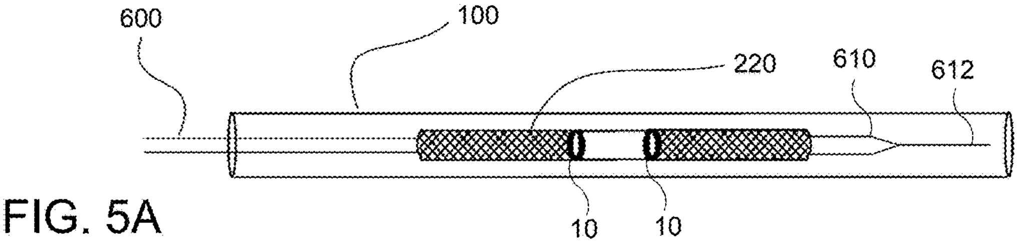
FIGS. 5A and 5B are a stent deployment catheter with collapsed stent and deployed stent.
Figure 5B:
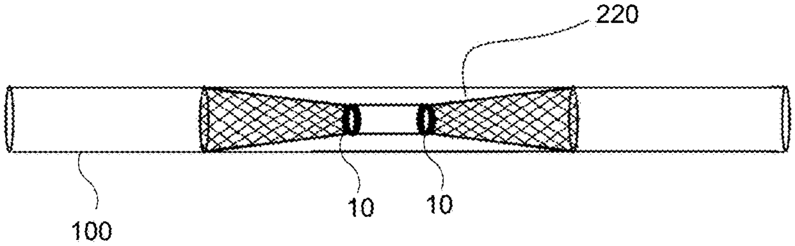

FIG. 5A illustrates a stent deployment catheter 600 with collapsed stent 220 and deployed stent. This is but one possible system for deployment. The catheter 600 is placed inside the vessel and advances to the deployment location. The stent 220 includes the bands 10 which form the restriction. The catheter is inserted into a vessel or a shunt tube 100 and the stent 220 positioned to a location at which the stent will be placed. Element 100 may be a shunt tube or a vessel of a patient. In this embodiment, the stent 220 is secured to a balloon 610 which is guided by a wire 612. When the balloon is expanded, as shown in FIG. 5B, the stent 220 is secured to the wall of the vessel to maintain itself in place. The outer ends of the stent 220 expand while the restricted portion between the bands 10 does not expand and thus forms the restricted section. The center area of the balloon 610 may not expand thus leaving the narrow area between the bands un-expanded.

FIG. 6 illustrates an unexpanded balloon 40 in connection with a catheter 600 and an expanded balloon 45 in connection with a catheter 600. Catheter based balloons are understood by those of ordinary skill in the art and as such are not described in detail herein.

Once created or deployed various clinical situations may dictate modification of the restrictor whether permanent or temporary. The modification may include the diameter of the restriction or the length of the restricted section. Thus, the design anticipates the need to alter the restrictor once placed. The restrictor, bands 10 may be altered with various materials depending on the clinical situation and hence the restrictors bands may be expandable, fracturable or elastic. In some embodiments, the restrictor bands 10 return, or can be manipulated to return, to a narrower diameter after being expanded.

As shown in FIG. 7A through 7E, the expandable restrictor is described where the non-expanded restrictor band 10 is first used within the shunt FIG. 7A to create a restricted section 110 in the shunt tube 100. When clinically needed a balloon 40 can be passed using endovascular technique into the center section of the restrictor band 10. Once the balloon 40 is inflated to become an inflated balloon 45, the restrictor band 10 is stretched as shown in FIG. 7C. When the balloon is deflated as shown in FIG. 7D and removed, the restrictor band 10 maintains its expanded shape as shown in FIG. 7E. This system allows a narrowing to be established in the tube through which blood flows and then if needed, remove the restriction to restore unrestricted blood flow. All this may occur with minimally invasive catheter and balloon techniques.

Figure 8A:
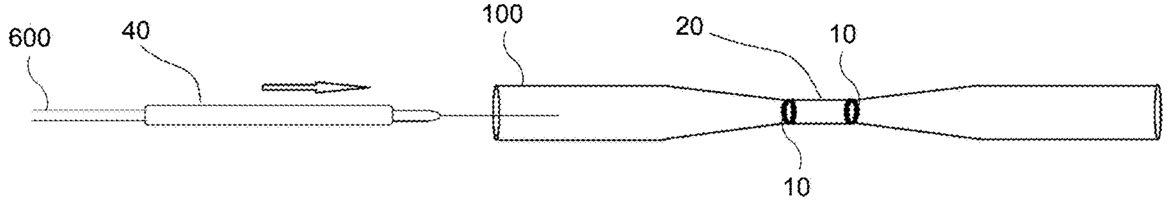
FIG. 8A is an illustration of a deflated balloon advancing into graft with long flow restrictor.
Figure 8B:
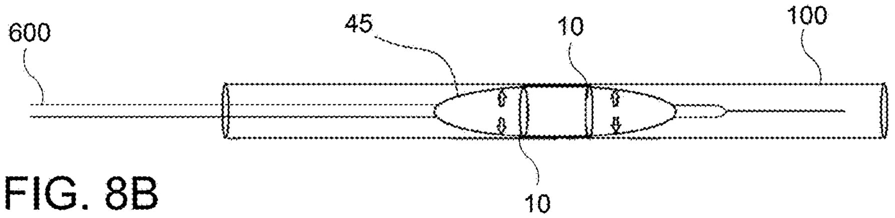
FIG. 8B is an illustration of an inflated balloon expanding long flow restrictor.
Figure 8C:
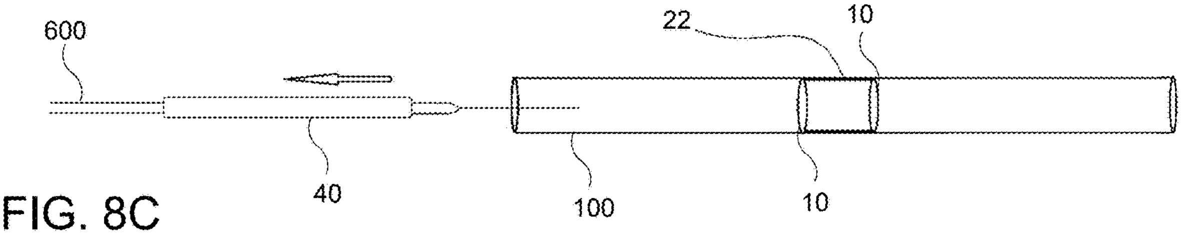
FIG. 8C is an illustration of a deflated balloon removal and expanded restrictor 20.

FIGS. 8A, 8B, and 8C illustrate a system and process as shown in FIG. 7A-7E but with an expanded restricted area formed by two restrictor bands 10. As compared to FIG. 7A-7E, similar elements are identified with identical reference numbers. In this embodiment, the expanded balloon 45 may have a wider area to expand both bands 10. This is similarly shown when the restrictor was initially deployed using the longer restrictor FIGS. 8A through 8C.

Figure 9A:
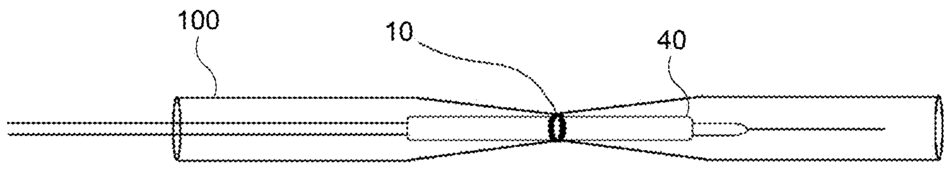
FIG. 9A is an illustration of a deflated balloon within flow restrictor.
Figure 9B:
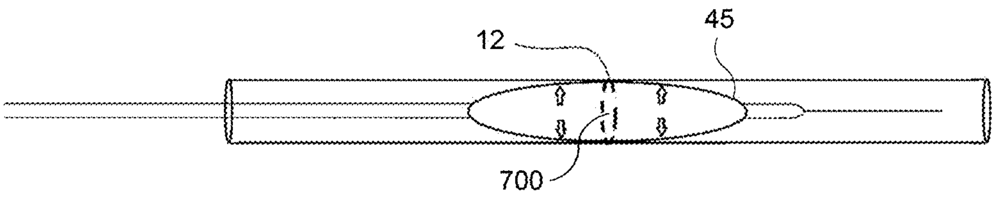
FIG. 9B is an illustration of an expanded balloon and fractured, expanded flow restrictor 10*a*.
Figure 9C:
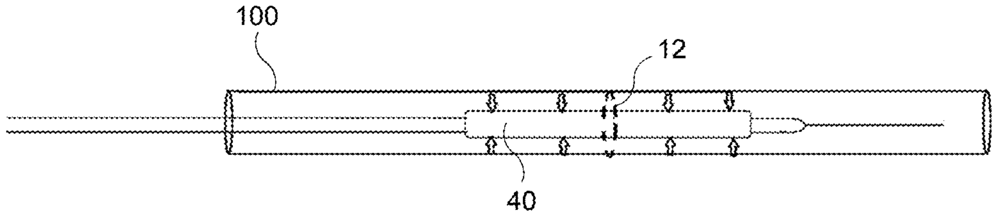
FIG. 9C is an illustration of a balloon deflated and expanded, fractured restrictor.
Figure 9D:
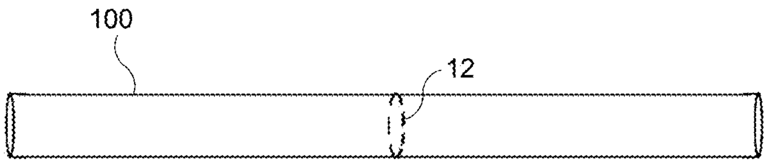
FIG. 9D is an illustration of a graft with expanded, fractured restrictor.

In a second embodiment, shown in FIGS. 9A through 9D, a fracturable restrictor band 10 is used again creating a narrowing within the shunt. When a balloon is passed and inflated within the fracturable restrictor, the ring fractures at fracture points 700 as shown in FIG. 9B. Preset fracture points 700 that break or fracture to allow the release of pressure and associated radial force existing tube, and previously restrained by the fracturable restrictor band 10. Once fractured, the band is referred to as a fractured band 12. As shown in FIG. 9C, the balloon 40 is deflated for removal and the fractured band 12 no longer creates a stenosis. Then, in FIG. 9D, the shunt tube 100 is unrestricted. This allows expansion of the shunt tube 100 eliminating the narrow area and blood flow resistance. This creates a permanent loss of narrowing.

A third embodiment of the material design is that of a resistor band 14 made of elastic materials. As shown in FIGS. 10A, 10B, 10C, 10D and 10E, the restrictor band 14 is created or deployed and once the need arises to alter the restrictor band 14 it is temporarily opened. As shown in FIG. 10C, the balloon 45 is inflated to expand the restrictor band 14. This expands the stenosis and based on the elasticity and properties of the restrictor band 14 the band may stay at a larger diameter for different periods of time. Once the balloon 40 is deflated, the elastic material of the restrictor band 14 reform to its original state again acting as a flow restrictor. The return to the narrow shape may occur rapidly or after a period of time. This may be useful when balloon angioplasty is needed in other parts of the shunt to help maintain patency, but the stenosis is still desired after the angioplasty. The elastic restrictor band 14 may be made of any material that is expandable and then returns to its narrowed diameter shape rapidly or slowly after expansion.

In one embodiment, the shunt is equipped with two or more fracturable restrictor bands such that one or more of the restrictor bands have a different diameter. In a basic embodiment, the first restrictor band has an inner diameter that is less than the inner diameter of the second restrictor band. Both are located around the outer surface of the shunt. In use, the shunt is paced in a patient which establishes a restriction or stenosis in the shunt thereby reducing blood flow. If, over time, it is determined that the restriction is too great, then a balloon may be directed through a blood vessel to the shunt and filled with gas or liquid to increase the diameter of the balloon. The diameter of the balloon may be increased sufficiently to fracture the first restrictor band, while leaving the second restrictor band unaffected. Thus, after fracturing the first restrictor band, the inner diameter of the opening is increased to the diameter of the second restrictor band. If the doctor again determines the blood flow restriction is too great, then a balloon may be inserted inside the second restrictor to fracture the second structure thereby again increasing the inner diameter of the shunt. This may occur with more than two restrictor bands to create additional degrees of control over the restriction size.

Figure 11:
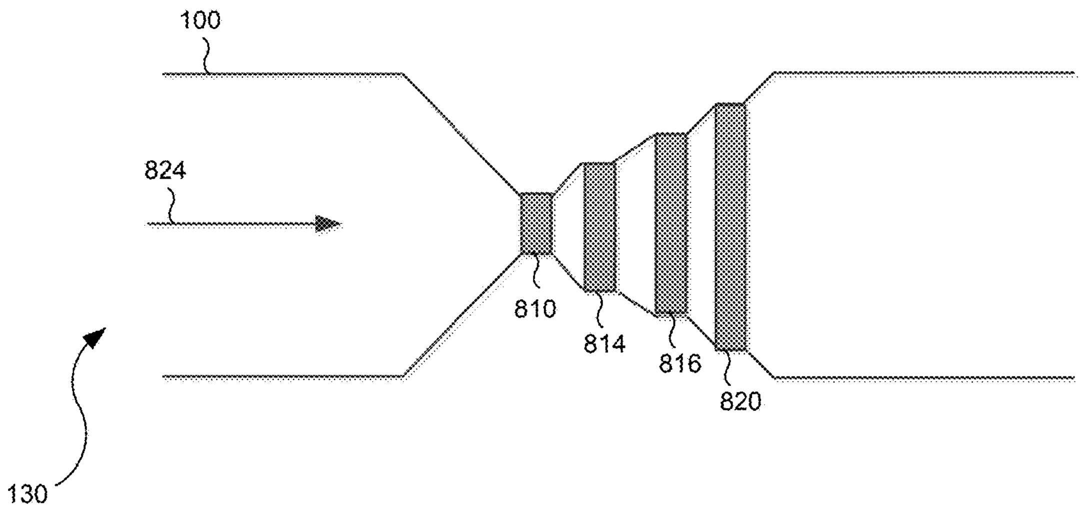
FIG. 11 illustrates one such embodiment that includes a stent tube having multiple bands of various diameters.

FIG. 11 illustrates one such embodiment that includes a stent tube having multiple bands of various diameters. This is but one possible configuration and as such other embodiments and configurations are possible, that which do not depart from the claims that follow. In this embodiment the shunt tube 100 includes an intake end configured to accept blood flow 824 as shown by the arrow. Any number of bands are possible but in this embodiment four bands 810, 814, 816, 820 are shown. A first band 810 has the smallest diameter, referred to herein as a first diameter. A second band 814 has a diameter greater than the first band 810, referred to herein as a second diameter. A third band 816 has a diameter greater than the second band 814, referred to herein as a third diameter. A fourth band 820 has a diameter greater than the third band 816, referred to herein as a fourth diameter.

In operation, a balloon (not shown) or other expansion device, may be inserted into the tube 100 and expanded sufficiently to fracture or otherwise expand the first band 810 thereby changing the diameter of the stenosis from the first diameter to the second diameter. If that stenosis is too small, then the process can be repeated at a later time to break the second band 814. This process may repeat to provide adjustability in the amount of narrowing in the stenosis including no narrowing by breaking all bands.

Figure 12:
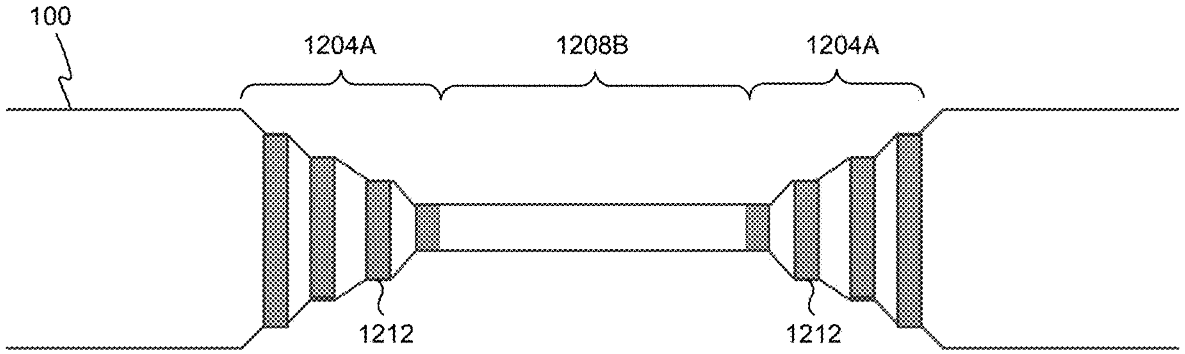
FIG. 12 illustrates an embodiment with a mirror set of bands.

FIG. 12 illustrates an embodiment with a mirror set of bands. The first set of bands 1204A is duplicated with a second set of bands 1204B. The bands may be separated by a separation distance 1208. Operation of this embodiment is as described above. The number of bands may vary from embodiment to embodiment. The value of the separation distance 1208 may vary to control blood flow dynamics as described herein. As the bands 1212 are broken, expanded, stretched, or separated, the tube will expand outward to a diameter determined by the band of the smallest diameter.

Figure 13:
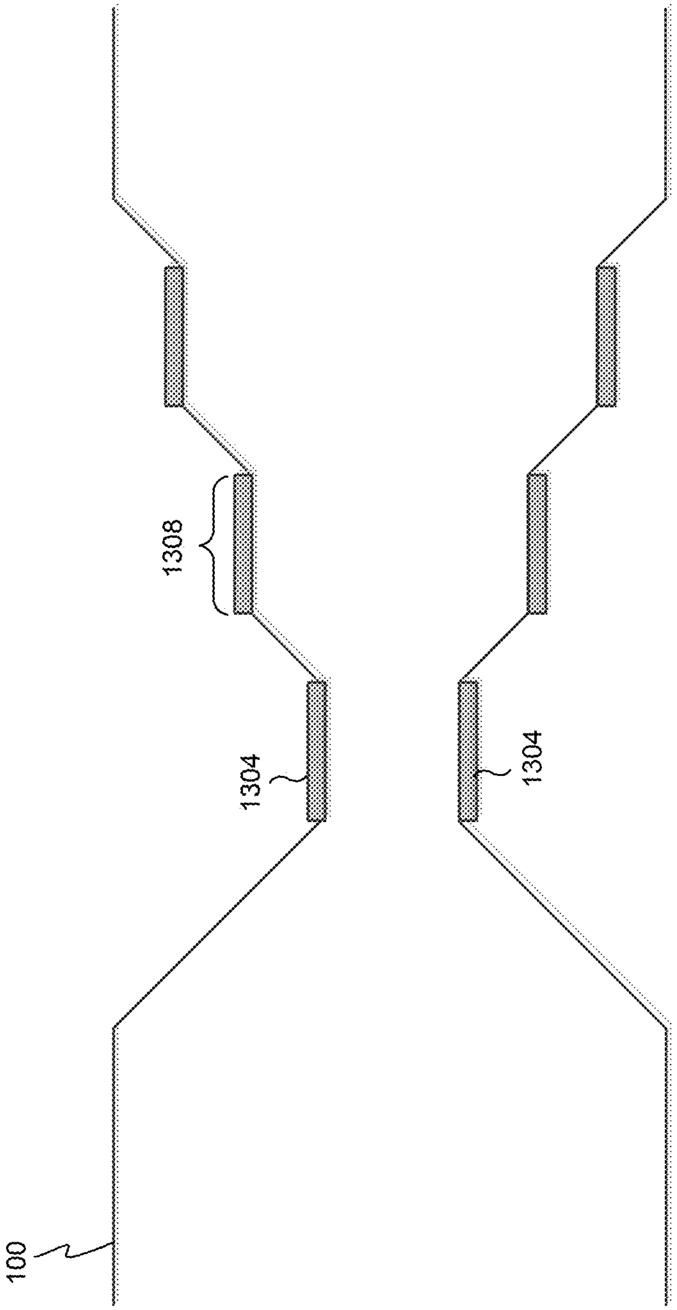
FIG. 13 illustrates an embodiment with bands having a greater width.

FIG. 13 illustrates an embodiment with bands having a greater width. It is also contemplated that the length of the stenosis may be determined by the width of the band. As such, the bands may be of different thickness or width. As shown in FIG. 13, the bands 1304 shown in cross section, are wider than those shown in the other embodiments. Varying the stenosis length 1308 will adjust blood flow dynamics. As with the other embodiments shown and described herein, the bands may be expanded to adjust the diameter of the stenosis. It is also contemplated that the width of each band may vary even for a single shunt tube 100. Thus, one band may be narrow, the next band wide, and the next band wider. Thus, each band would establish a different stenosis length.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A dialysis stent with an expandable restriction, the dialysis stent being configured for use with an arterial venous (AV) fistula or graft in a manner wherein the AV fistula or graft connects an artery of a patient to a vein of the patient, and configured for treating renal disease in the patient, comprising:

a shunt tube having an inlet end and an outlet end and configured to be deployed within the AV fistula or graft, the shunt tube having a central opening which extends from the inlet end to the outlet end such that the central opening has a first diameter; and at least one elastic band configured to narrow the central opening of the shunt tube and thereby create a stenosis in the shunt tube that acts as a flow restrictor for allowing the shunt tube to elastically shunt blood flow from an extremity of the patient, the at least one elastic band extending around a portion of the shunt tube and located between the inlet end and the outlet end without folding of the at least one elastic band, the at least one elastic band creating a reduced diameter section of a second diameter in the shunt tube that is elastically adjustable from the second diameter, which is less than the first diameter, to a third diameter that is greater than the second diameter such that the stenosis expands when the shunt tube moves from having the second diameter to having the third diameter, the at least one elastic band exerting radial pressure on the shunt tube toward having the second diameter both when the shunt tube has the second diameter and when the shunt tube has the third diameter, the at least one elastic band configured to elastically adjust from the second diameter to the third diameter responsive to a balloon inflating to expand the at least one elastic band, and from the third diameter back to the second diameter responsive to the balloon subsequently deflating, the at least one elastic band elastically reforming from an expanded state to an original state when adjusting from the third diameter back to the second diameter, the at least one elastic band being made of an elastic material different than a material of the shunt tube in order to create a radially inward pressure on the shunt tube and to allow the shunt tube to have smooth inner and outer surfaces proximate the at least one elastic band.

2. The stent of claim 1, wherein the at least one elastic band that is adjustable from the second diameter is reactive to outward pressure from within the shunt tube toward the at least one elastic band that causes the at least one elastic band to expand, thereby eliminating or increasing a diameter of the restriction to establish the shunt tube at a diameter greater than the second diameter during a clot clearing procedure.

3. The stent of claim 1, wherein the third diameter is the same as the first diameter.

4. The stent of claim 1, wherein the at least one elastic band is expandable from the third diameter to a fourth diameter, the fourth diameter greater than the third diameter.

5. The stent of claim 1, wherein the at least one elastic band has preset fracture points at predetermined sites that are configured to fracture before other locations of the band in order to allow the release of pressure and an associated radial force in response to pressure that expands the band beyond the first diameter thereby increasing the band from the second diameter to the third diameter.

6. The stent of claim 1, wherein the at least one elastic band comprises two or more restrictor bands of at least two different inner diameters, each of which is formed from an elastic material.

7. The stent of claim 1, wherein the at least one elastic band returns to the second diameter after a period of time sufficient to provide time for the shunt tube to have a clot removed therefrom.

8. The stent of claim 1, wherein the shunt tube is configured to adjust from the second diameter to the third diameter without the at least one elastic band being stitched to the shunt tube.

9. The stent of claim 1, wherein the shunt tube is configured to elastically adjust from the third diameter back to the second diameter without an additional medical procedure in a manner wherein the at least one elastic band is a sole force for radially contracting the shunt tube back to the second diameter.

10. The stent of claim 1, wherein the shunt tube and the at least one elastic band each have a middle disposed midway between the inlet and outlet ends of the shunt tube.

11. The stent of claim 1, wherein, when the shunt tube adjusts from the second diameter to the third diameter, the shunt tube radially expands outwardly.

12. The stent of claim 1, wherein the shunt tube is configured to elastically adjust from the third diameter back to the second diameter without an additional medical procedure in a manner wherein the at least one elastic band is a sole force for radially contracting the shunt tube back to the second diameter, wherein the shunt tube is configured to adjust from the second diameter without the at least one elastic band being stitched to the shunt tube, wherein the shunt tube and the at least one elastic band each have a middle disposed midway between the inlet and outlet ends of the shunt tube, and wherein, when the shunt tube is configured to adjust from the second diameter to the third diameter, the shunt tube radially expands outwardly.

13. The stent according to claim 6, wherein the two or more restrictor bands each have a different corresponding width.

14. The stent according to claim 6, wherein the two or more restrictor bands each have a different corresponding thickness.

15. A dialysis stent with an expandable restriction, the dialysis stent being configured for use with an arterial venous (AV) fistula or graft in a manner wherein the AV fistula or graft connects an artery of a patient to a vein of the patient, and configured for treating renal disease in the patient, comprising:

a shunt tube having an inlet end and an outlet end and configured to be deployed within the AV fistula or graft, the shunt tube having a central opening which extends from the inlet end to the outlet end such that the central opening has a first diameter; and at least one elastic restrictor configured to narrow the central opening of the shunt tube and thereby create a stenosis in the shunt tube that acts as a flow restrictor for allowing the shunt tube to elastically shunt blood flow from an extremity of the patient, the at least one elastic restrictor extending around a portion of the shunt tube and located between the inlet end and the outlet end without folding of the at least one elastic restrictor, the at least one elastic restrictor creating a reduced diameter section of a second diameter in the shunt tube that is elastically adjustable from the second diameter, which is less than the first diameter, to a third diameter that is greater than the second diameter such that the stenosis expands when the shunt tube moves from having the second diameter to having the third diameter, the at least one elastic restrictor exerting radial pressure on the shunt tube toward having the second diameter both when the shunt tube has the second diameter and when the shunt tube has the third diameter.

16. The stent according to claim 1, wherein the at least one elastic restrictor is configured to narrow the central opening of the shunt tube and thereby create the stenosis in the shunt tube such that the stenosis is disposed midway between the inlet end of the shunt tube and the outlet end of the shunt tube.

* * * * *